US00PP11562P

United States Patent [19]

Zary

[11] Patent Number: Plant 11,562

[45] Date of Patent: Oct. 10, 2000

[54] FLORIBUNDA ROSE PLANT NAMED 'JACSHOK'

[75] Inventor: Keith W. Zary, Thousand Oaks, Calif.

[73] Assignee: Bear Creek Gardens, Inc., Medford, Oreg.

[21] Appl. No.: 09/255,436

[22] Filed: Feb. 22, 1999

[51] Int. Cl.[7] ..... A01H 5/00

[52] U.S. Cl. ..... Plt./149

[58] Field of Search ..... Plt./141, 148, 149, Plt./150

*Primary Examiner*—Howard J. Locker

*Attorney, Agent, or Firm*—Klarquist Sparkman Campbell Leigh & Whinston, LLP

[57] ABSTRACT

Floribunda rose plant having lavender-pink flowers; strong lemon fragrance; resistance to powdery mildew and rust; vigorous, upright plant habit; continuous bloom, and flowers produced in clusters.

1 Drawing Sheet

The present invention relates to a new and distinct variety of rose plant of the floribunda class which was originated by me by crossing an unnamed seedling ('MORchari', U.S. Plant Pat. No. 5,975×'TINherb' (also known as 'Herbie'), U.S. Plant Pat. No. 6,787), with the variety 'KORblue', U.S. Plant Pat. No. 3,846.

The primary objective of this breeding was to a new rose variety having lavender to lavender-pink flowers, strong fragrance, disease resistant foliage, vigorous, upright plant habit, rapid repeat bloom, and flowers produced in clusters. The objective was substantially achieved, along with other desirable improvements, as evidenced by the following unique combination of characteristics that are outstanding in the new variety and that distinguish it from its parents, as well as from all other varieties of which I am aware:

1. Strong flower fragrance;
2. Dark green, glossy foliage;
3. Upright, vigorous growth;
4. Lavender-pink flowers;
5. Flowers produced in clusters;
6. Resistance to powdery mildew and rust.

Asexual reproduction of this new variety by budding, as performed at Wasco, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling ('MORchari', U.S. Plant Pat. No. 5,975×'TINherb' (also known as 'Herbie'), U.S. Plant Pat. No. 6,787).

*Pollen parent.*—'KORblue' (U.S. Plant Pat. No. 3,846).

Classification:

*Botanical.*—*Rosa hybrida.*

*Commercial.*—Floribunda.

FLOWER

Observations made from specimens grown in a garden environment at Somis and Wasco, Calif., March 1997 to December 1998.

Blooming habit: Continuous.

Bud:

*Size.*—One and one-quarter inches long when the petals start to unfurl.

*Form.*—The bud form is long, pointed ovoid.

*Color.*—When sepals first divide, bud color is Red-Purple Group 66C. When half blown, the upper side of the petal is Red-Purple Group 66C on the outer three-quarters of the petal; the inner one-quarter of each petal is White Group 155D. The lower side of the petal is Red-Purple Group 66C to Red-Purple Group 66D on the outer three-quarters of the petal and White Group 155D on the inner one-quarter.

*Sepals.*—Color: Green Group 138B. Surface texture: Covered in fine hairs. There are three lightly appendaged sepals. There are two unappendage sepals with hairy edges.

*Receptacle.*—Color: Green Group 137D with a blush of Greyed-Red Group 181B when exposed to bright sun. Shape: Funnel. Size: Small, about ¼"×¼". Surface: Smooth.

*Peduncle.*—Length: Medium, averaging about two and one-half inches to three inches. Surface: Glandular. Color: Yellow-Green Group 146C with some Greyed-Red Group 181B in areas exposed to bright sun. Strength: Stiff, erect.

Bloom:

*Size.*—Medium. Average open size is three and one-half inches.

*Borne.*—Singly and several together in pyramidal clusters of three to seven blooms.

*Stems.*—Strength: Strong. Average length is about fourteen to eighteen inches.

*Form.*—When first open: High-centered. Permanence:. Flattens, outer petals curl back.

*Petalage.*—Number of petals under normal conditions: 25–30.

*Color.*—The upper sides of the petals are Red-Purple Group 66C on the outer three-quarters of the petal, the inner one-quarter of the petal is White Group 155D. The reverse sides of the petals are Red-Purple Group 66C to Red-Purple Group 66D on the outer three-quarters of the petal, the inner one-quarter of the petal is White Group 155D. The base of each petal has a small (⅛"×⅛"), Yellow-Orange Group 18C color spot on both surfaces. The major color on the upper side is Red-Purple Group 66C.

*Variegations.*—None.

*Discoloration.*—The general tonality at the end of the first day: No change. At the end of the third day: No change. By day four or five, there is a general fading from Red-Purple Group 66C to Red-Purple Group 66D on both petal surfaces.

*Fragrance*.—Strong, lemon.

Petals:

*Texture*.—Thin.

*Shape*.—Oval to deltoid.

*Form*.—Tips slightly recurved.

*Arrangement*.—Imbricated. Petaloids in the center: Few (0–3). Color is Red-Purple Group 66C with an occasional White Group 155B streak on the petaloid. Sizes vary from ⅛" to ¼" wide and ¼" to ½" long.

*Persistence*.—Petals drop off cleanly before drying.

*Lastingness*.—On the plant: Fair (five to six days). As a cut flower: Fair (about six to seven days).

Reproductive parts:

*Anthers*.—Size: Medium. Quantity: Many. Color: Yellow-Orange Group 22C. Arrangement: Regular around styles.

*Filaments*.—Color: Yellow Group 5D.

*Pollen*.—Present.

*Styles*.—Color: Greyed-Purple Group 184D.

*Stigmas*.—Color: Orange-White Group 159D.

Plant:

*Form*.—Bush.

*Growth*.—Vigorous, upright, branching. Mature plant height is about three and one-half feet, width is about two and one-half feet.

Foliage: Number of leaflets on normal mid-stem leaves: Five or seven

*Size*.—Large (5½ to 6" long×3½–4" wide).

*Quantity*.—Abundant.

*Color*.—New foliage: Upper surface: Greyed-Orange Group 176A. Lower surface: Greyed-Orange Group 176B. Old foliage: Upper surface: Green Group 139A. Lower surface: Green Group 139C.

Leaflets:

*Shape*.—Pointed oval.

*Texture*.—Leathery, glossy.

*Edge*.—Serrated.

*Serration*.—Single, small.

*Petiole rachis*.—Lower: Green Group 138C. Upper: Green Group 138A.

*Petiole underside*.—Rough with prickles.

*Stipules*.—Short (⅜"–½"), serrated, bearded.

*Disease resistance*.—Resistant to mildew and rust under normal growing conditions. Susceptible to blackspot.

Wood:

*New wood*.—Color: Greyed-Orange Group 176A. Bark: Smooth.

*Old wood*.—Color: Green Group 137C. Bark: Smooth.

Prickles:

*Quantity*.—On main canes from base: Ordinary. On laterals from main canes: Ordinary.

*Form*.—Medium, hooked downward.

*Color when young*.—Greyed-Red Group 181B.

*Color when mature*.—Greyed-Orange Group 177D.

Small Prickles:

*Quantity*.—On main stalks: None. On laterals: None.

I claim:

1. A new and distinct variety of rose plant of the floribunda class, substantially as herein shown and described, characterized particularly by its lavender-pink flowers; strong lemon fragrance; resistance to powdery mildew and rust; vigorous, upright plant habit; continuous bloom, and flowers produced in clusters.

* * * * *

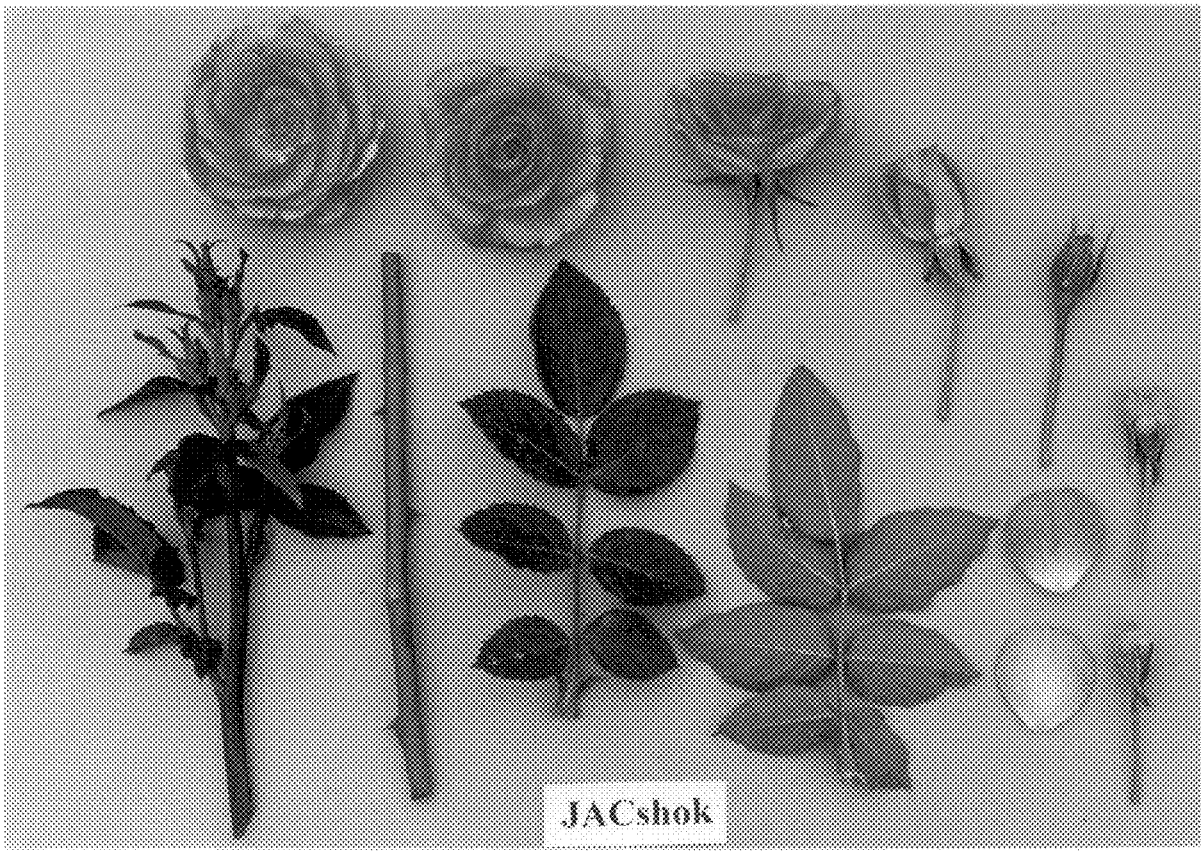
JACshok